United States Patent
Rapp et al.

(10) Patent No.: US 7,335,332 B2
(45) Date of Patent: Feb. 26, 2008

(54) METHOD AND APPARATUS FOR TREATING DIGESTIBLE AND ODIFEROUS WASTE

(76) Inventors: Gary L. Rapp, R.R. #1, Box 177, Athens, IL (US) 62613; Carrie L. Rapp, R.R. #1, Box 177, Athens, IL (US) 62613

( * ) Notice: Subject to any disclaimer, the term of this patent is extended or adjusted under 35 U.S.C. 154(b) by 696 days.

(21) Appl. No.: 10/431,291

(22) Filed: May 7, 2003

(65) Prior Publication Data

US 2003/0198569 A1 Oct. 23, 2003

Related U.S. Application Data

(63) Continuation-in-part of application No. 09/678,064, filed on Oct. 2, 2000, now Pat. No. 6,602,464.

(60) Provisional application No. 60/197,270, filed on Apr. 14, 2000.

(51) Int. Cl.
*A61L 9/14* (2006.01)
(52) U.S. Cl. ............................ 422/5; 422/41; 422/42
(58) Field of Classification Search .................. 422/5, 422/41, 42; 137/15.04, 15.05
See application file for complete search history.

(56) References Cited

U.S. PATENT DOCUMENTS

| | | | |
|---|---|---|---|
| 3,639,258 A | 2/1972 | Corino et al. | 252/316 |
| 4,007,262 A | 2/1977 | Bowers | 424/76 |
| 4,210,680 A * | 7/1980 | Dawson et al. | 426/641 |
| 4,244,061 A | 1/1981 | Webster et al. | 4/144.1 |
| 4,264,760 A | 4/1981 | Meyer | 528/230 |
| 4,641,605 A | 2/1987 | Gordon | 119/1 |
| 4,821,677 A | 4/1989 | Harrison | 119/1 |
| 5,772,722 A | 6/1998 | Gednalske et al. | 71/21 |
| 5,962,001 A | 10/1999 | Rose et al. | 424/404 |
| 6,602,464 B1 * | 8/2003 | Rapp et al. | 422/5 |

FOREIGN PATENT DOCUMENTS

| DE | 2296514 A | 7/1996 |
|---|---|---|
| JP | 58013817 A | 1/1996 |

(Continued)

OTHER PUBLICATIONS

Advertisement for Barrier Odor Migration Aid, Nov. 2000.

(Continued)

*Primary Examiner*—Gladys J P Corcoran
*Assistant Examiner*—Sean E. Conley

(57) ABSTRACT

A method is provided for minimizing the emissions of odorous gases and neutralizing volatile fatty acids generated by anaerobic decomposition of digestible and odiferous animal waste that includes the step of adding an alkaline solution to the digestible and odiferous animal waste to at least partially neutralize volatile fatty acids present in the digestible and odiferous animal waste and applying a layer of oil and activated carbon to the surface of the waste. A system for applying the above method includes means for applying the layer of oil and activated carbon to a surface of the waste; means for injecting the alkaline solution into the waste below the layer of oil and activated carbon; means for monitoring the pH level of the waste; and means for triggering the injection of additional alkaline solution when the pH level of the waste reaches a set point.

12 Claims, 9 Drawing Sheets

FOREIGN PATENT DOCUMENTS

JP          10167866 A      6/1998

OTHER PUBLICATIONS

Clanton et al., "Experimental Manure Storage Covers for Odor Control", www.BAE.UMM.EDU/ANNRPT/1997/RESEARCH/ORDER5.HTML.

Camberato et al., "Land Application of Animal Manure", HTTP://HUBCAP.CLEMSON.EDU/-BLPPRT/MANURE.HTML (1996).

Options for Managing Odor: A Report from the Swine Odor Task Force, Mar. 1, 1995, p. 27 and Chapter 5, Odor Control (from same book), 5-28 & 5-29.

J. A. Zahn, et al., "Characterization of Volatile Organic Emissions and Wastes from a Swine Production Facility", *J. Environ. Qual.*, 26, 1687-1696 (1997).

C. J. Clanton, et al., "Swine Manure Storage Covers for Odor Control", *Applied Engineering in Agriculture*, 15(5), 567-572 (1999).

S.J. Troyer, et al., "Effects of Ammonia Inhibition on the Anaerobic Sequencing Batch Reactor", Hazardous and Industrial Wastes- Proceedings of the Mid Atlantic Industrial Wastes- Conference 1997, pp. 12-21.

A. William, "Reducing Losses of Ammonia From Slurry With Floating Covers", SRI On-Line.

\* cited by examiner

METHOD AND APPARATUS FOR TREATING DIGESTIBLE AND ODIFEROUS WASTE

CROSS-REFERENCES

This application is a continuation-in-part of U.S. application Ser. No. 09/678,064 filed 2 Oct. 2000, now U.S. Pat. No. 6,602,464 which claims the priority of provisional application Ser. No. 60/197,270, filed 14 Apr. 2000.

TECHNICAL FIELD

The present invention relates generally to the field of wastewater treatment and, more particularly, to a method and apparatus for dealing with odors emitted by organic animal waste.

DESCRIPTION OF THE RELATED ART

Over the past decades there has been a shift from smaller localized family farms toward larger integrated confinement agricultural operations. Large agricultural operations typically utilize confinement barns to house a large number of livestock such as swine. It is not uncommon for hog-confinement operations to be grouped in close proximity, forming "mega-farms" which may house tens of thousands of hogs. While these larger agricultural operations have numerous advantages, they also encounter significant pollution problems arising from the handling and treatment of manure and wastewater. Pollution problems associated with liquid animal waste include waste solids, bacteria and foul odors that result from anaerobic digestion. Environmental concerns more specifically center on odor and water quality issues.

Currently, for treatment of animal wastes and wastewater most agricultural facilities use anaerobic digestion, i.e. anaerobic bacteria consume some or much of the organic waste. The primary reason for using anaerobic digestion is that it is natural, but it also has the advantages of simplicity and low cost. Wastewater is simply discharged from the animal storage facility into one or more open lagoons where the waste undergoes natural anaerobic digestion. However, noxious gases including ammonia, hydrogen sulfide, volatile fatty acids, and indoles may be emitted from anaerobic lagoons at hog farms as well as within the animal storage facilities. Additionally, the time required for complete digestion of the organic wastes is relatively long, typically lasting from weeks to months. Some current regulations require a residence time of 180 days for animal waste facilities using anaerobic lagoons for digestion. Odors emanating from lagoons, confinement houses, and fields onto which wastes are sprayed create a nuisance. In fact, as a result of odor problems associated with anaerobic lagoons, some states have legally mandated buffer zones or designated land areas between lagoon sites and populated areas. In addition, the noxious gases produced by animal waste create a potentially hazardous environment in animal storage facilities for humans working in such facilities and the animals housed in these facilities.

Continuing efforts are being made to improve agricultural and animal waste treatment methods and apparatus. For example, one process known in the art is the transformation of animal waste wherein solids are precipitated in a solids reactor, the treated slurry is passed to a bio-reactor zone where soluble phosphorus is precipitated with metallic salts, the slurry is aerobically and anaerobically treated to form an active biomass. The aqueous slurry containing bio-converted phosphorus is passed into a polishing eco-reactor zone wherein at least a portion of the slurry is converted to a beneficial humus material. However, in operation, the system requires numerous chemical feeds and a series of wetland cells comprising microorganisms, animals and plants.

Several studies done in the past several years have also addressed the issue of reducing odors by covering manure storage units. For example, many types of natural floating covers formed by fibrous materials have been used to reduce manure odor. Artificial floating crusts have consisted of chopped straw, plastic foam pellets, a combination of straw and pellets, mats, or tarpaulins. Tight covers have included plastic covers sealed at the edge and light constructed roofs. These types of covers have proven to be inadequate for several reasons. Such covers have not sufficiently eliminated odorous emissions. Also, such covers cannot be efficiently utilized in an animal storage facility, where the pit must remain open to receive waste as it is generated by the housed animals. Natural floating covers have also been known to fail under conditions such as rainy weather, which causes the floating crusts to become submerged in the waste.

The present invention is directed to overcoming one or more of the problems set forth above.

SUMMARY OF THE INVENTION

An aspect of the present invention is to provide a method of reducing emission of odiferous gasses that is capable of one or more of the following: stopping the evaporation of liquids beneath the surface of the treatment to reduce the humidity levels in animal storage facilities, maintaining higher air quality in animal storage facilities, establishing an aqueous alkaline, anaerobic environment, and liquefying waste solids through anaerobic bacterial activity.

In accordance with the above aspect of the invention, there is provided a method for treating digestible and odiferous animal waste in a containment system to minimize odors that includes the step of adding an alkaline solution to the digestible and odiferous animal waste to at least partially neutralize volatile fatty acids present in the digestible and odiferous animal waste. The alkaline solution includes a mixture of about 7.2% ammonia and the remainder water in applications where the pH level of the waste is regularly monitored. In other applications, the alkaline solution advantageously includes a mixture of about 3.2% ammonium chloride, about 7.2% ammonia, and the remainder water. In an alternate embodiment, the method further includes the step of applying a layer of oil to the surface of the digestible and odiferous animal waste. In yet another embodiment, a layer of oil and activated carbon is applied to the surface of the waste.

A system for treating digestible and odiferous animal waste in a containment system includes means for applying a layer of a mixture of oil and activated carbon to a surface of the waste; means for injecting an alkaline solution into the digestible and odiferous animal waste below the layer of oil and activated carbon; means for monitoring the pH level of the waste; and means for triggering the injection of additional alkaline solution when the pH level of the waste reaches a set point, said means for triggering communicating with the means for monitoring and the means for injecting.

This aspect is merely illustrative of the innumerable aspects associated with the present invention and should not be deemed as limiting in any manner. These and other aspects, features and advantages of the present invention will become apparent from the following detailed description when taken in conjunction with the drawings.

BRIEF DESCRIPTION OF THE DRAWINGS

Reference is now made to the drawings which illustrate the best known mode of carrying out the invention and wherein the same reference numerals indicate the same or similar parts throughout the several views.

DETAILED DESCRIPTION

Figure 1:
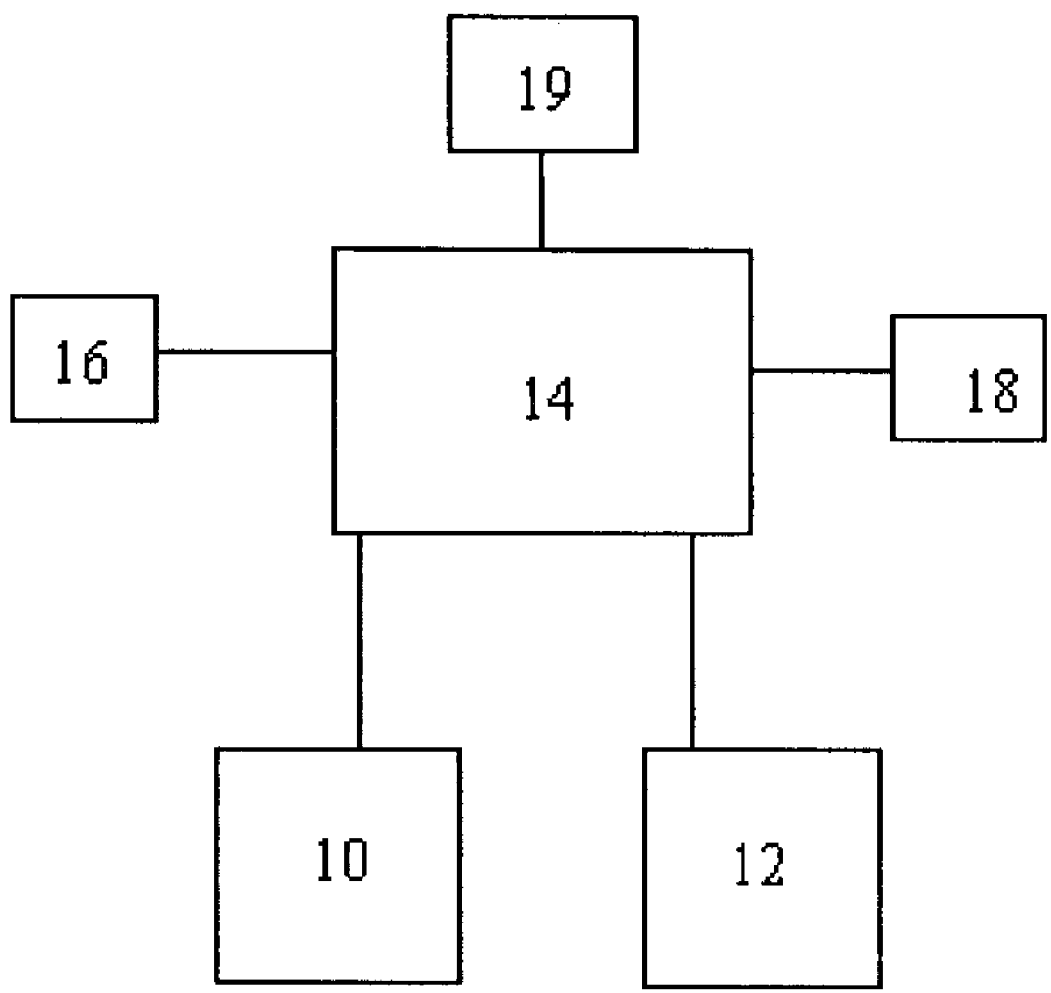
FIG. 1 is a schematic view of a system for treating digestible and odiferous animal waste in a containment system utilizing an alkaline solution.

A system and/or process according to embodiments of the present invention includes injecting alkaline solution into digestible waste contained in a storage facility. The base alkaline solution is preferably a mixture including ammonia ($NH_3$) and water. The relative percentages of the ingredients in the alkaline solution advantageously include between about 6.5% and 7.9% ammonia and the remainder water, although, in applications where the pH level of the waste is continually monitored, the amount of ammonia in the alkaline solution can be increased up to 29%. In a preferred embodiment, the solution includes about 7.2% ammonia and the remainder water. The alkaline solution creates an acid/base reaction with volatile fatty acids present in the fecal matter present in the waste. These volatile fatty acids, including acetic acid, propionic acid, butanoic acid, hexanoic acid and heptanoic acid, are by-products of the anaerobic digestion process of bacteria in the waste. The alkaline solution neutralizes these volatile fatty acids without destroying the bacteria or otherwise interrupting the actual decomposition process. This allows the microbial decomposition process to continue unabated, thereby effectively eliminating the odiferous by-products. Advantageously, the pH range of the waste is maintained between about 7.5 and 8.0. Above a pH of 8.0, the anaerobic bacteria, which are essential to decomposition, could become threatened by excessive alkalinity.

Advantageously, the alkaline solution is added into waste in smaller amounts on a regular basis and the pH level of the waste is monitored. This method of application minimizes the risk of the alkaline solution raising the pH level of the waste above a level that is safe for the anaerobic bacteria responsible for the decomposition process. An alternate embodiment of the alkaline solution includes a buffering component. The buffering component is preferably an ammonium salt, such as ammonium chloride or ammonium nitrate. This formulation of the alkaline solution is recommended for applications in which the alkaline solution is applied in a single large injection and if the pH of the waste is not continually monitored. The buffering component prevents the alkaline solution from excessively elevating the pH level of the waste and thereby creating an inhospitable environment for the anaerobic bacteria.

In accordance with another embodiment, it has been found that a layer of oil covering the surface of the waste storage pit or lagoon effectively reduces the offensive odors. In an alternate embodiment, a mixture of oil and activated carbon is applied to the surface of the waste. For convenience this layer is sometimes hereafter referred to as an "oil seal". The oil seal slows the transmission of oxygen ($O_2$) into the waste slurry to help maintain an anaerobic environment that is advantageous for digestion of the organic waste. The oil seal also prevents ammonia present in the waste and the alkaline solution from escaping into the atmosphere above the waste pit. The oil is preferably a vegetable oil, such as corn oil. Silicone oil may also be used. The oil to activated carbon ratio is preferably approximately 128:1. The alkaline solution is applied beneath the surface of the oil/activated carbon layer, to control the pH of the waste and to reduce the concentration of fatty acids and hydrogen sulfide ($H_2S$). The base in the alkaline solution neutralizes the fatty acids and hydrogen sulfide to less volatile salts, which remain in the waste. Accordingly, the emission of $H_2S$ and other odorous gases is significantly lowered. The vegetable oil is applied at a thickness, preferably a layer of at least one quarter (¼") to one (1") inch, that more or less provides a seal above the animal waste when applied. The activated carbon provides a trap for gases emitted from the animal waste located beneath the surface of the oil. If the oil/activated carbon layer is applied without the alkaline solution, the waste will continue to generate odiferous gases which will build up under and eventually penetrate the seal.

The alkaline solution neutralizes the volatile fatty acids present in the animal waste to their ammonium salts. These ammonium salts tend to be more water soluble and less volatile. Such reduction in volatility is important in the case of the malodorous volatile fatty acids of seven through three carbon atoms in chain length (heptanoic acid, hexanoic acid, pentanoic acid, butanoic acid, and propionic acid). Such odiferous volatile fatty acids are produced during the early stages of anaerobic digestion of proteins, fats, and oils. The alkaline solution does not destroy the microorganisms responsible for the anaerobic digestion by not allowing the waste slurry to get too alkaline. The desired pH range is about 7.5 to 8.0. This range also appears ideal for the other anaerobic microorganisms which complete the late stages of the digestion process reducing the carbon chain length to two (acetic acid and acetates) and converting the acetates to carbon dioxide ($CO_2$) and methane ($CH_4$). The alkaline solution thus performs two tasks: (1) neutralizing volatile fatty acids to their less volatile and more water soluble ammonium salts and (2) promoting the late stages of anaerobic digestion by maintaining ideal pH conditions for the responsible anaerobic microorganisms. The first task helps keep the odiferous volatile fatty acids, as well as $H_2S$, from escaping through the oil seal into the environment while the second task effectively removes the volatile fatty acids, and their salts, beneath the oil seal.

One preferred method for treating animal waste in a pit includes the step of first pumping the pit to the lowest level possible, using normal means of extraction that are well-known in the art. If pumping and delivering of the waste to an approved disposal area is not possible, the method can nonetheless be carried out without first pumping the pit. The next step is to apply preferably a one-quarter (¼") to one (1") inch layer of the oil/activated carbon mixture to the surface of the remaining waste in the pit. Next, the alkaline solution is injected below the oil/activated carbon layer. The pit is now ready to receive quantities of untreated waste. Once the waste reaches a maximum level in the pit, the waste may again by pumped from the pit. However, the oil/activated carbon will remain on the surface if the waste is pumped from the bottom of the pit. Thus, the need to apply an additional treatment of oil and activated carbon each time the pit is pumped is greatly reduced or eliminated.

It is important that the oil, activated carbon and alkaline solution are applied to the waste such that the waste is not agitated. Agitation of the waste beneath the surface layer causes gases and odors to be emitted, which has been known to result in death to livestock as well as humans. Therefore, it is advantageous to use an appropriate applicator or injector system in applying the treatment.

FIG. 1 illustrates a system suitable for application and maintenance of an oil seal/alkaline solution system to a waste storage facility, such as the waste pit in a livestock holding area. The system includes an injection system 10 for applying the oil seal to the surface of the waste and injecting the alkaline solution into the waste underneath the seal. A pH monitor 12 is installed in the facility and continuously monitors the pH level of the waste. A controller 14 communicates with both the pH monitor 12 and the injection system 10. The controller 14 monitors the pH level of the waste on a set schedule and computes the proper amount of base solution to add per injection cycle. This arrangement prevents an excess amount of base solution from being injected into the waste. The controller 14 can also be provided with a printer 16 in order to provide hourly reports of the pH levels monitored in the waste pit. The controller 14 may also have an alarm 18 to notify the operator of a malfunction in any part of the system. An air monitor 19 may also be incorporated into the system to continuously monitor the air quality of the facility.

Figure 2:
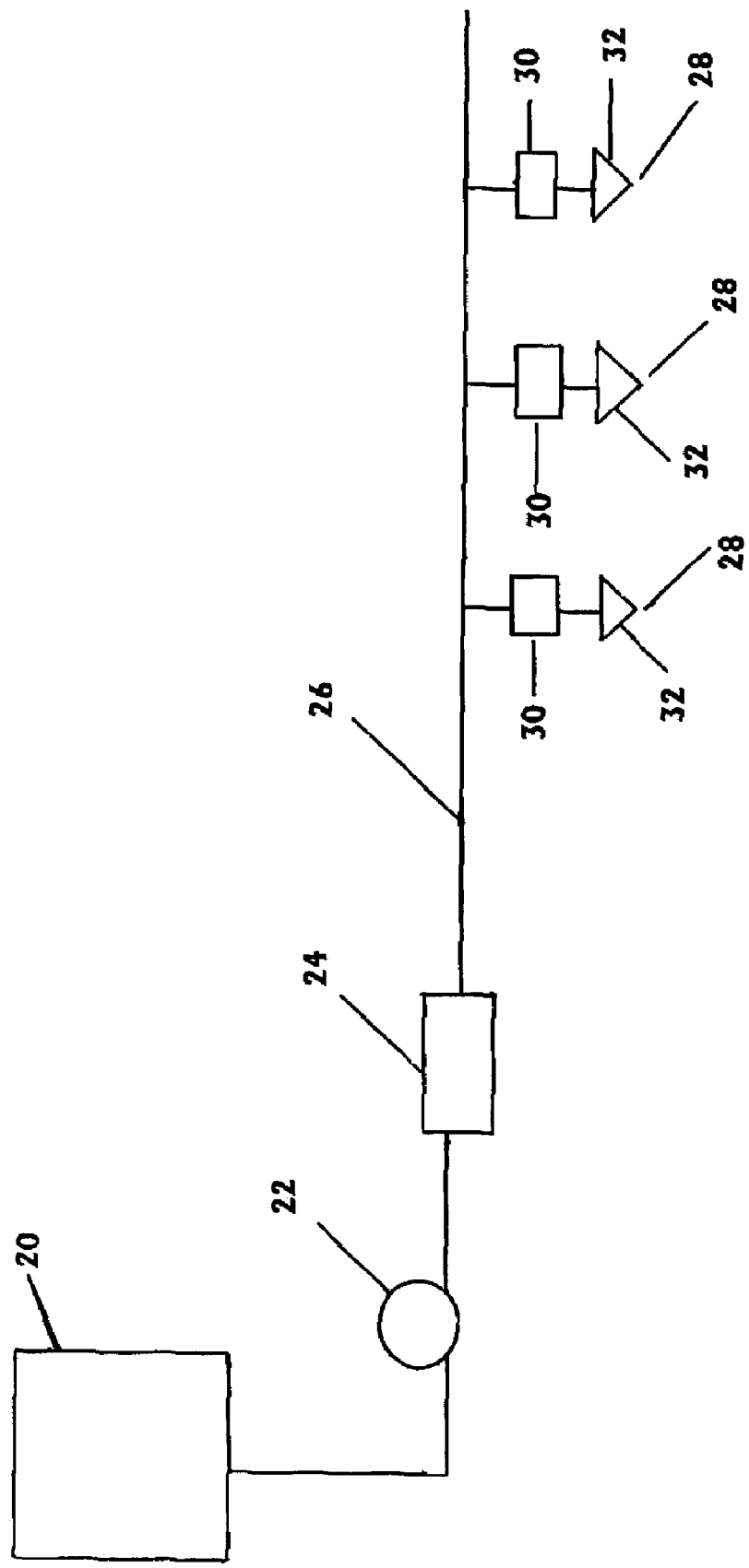
FIG. 2 is a schematic view of an injection system suitable for administering continuous injections of an odor control product as part of a method for treating digestible and odiferous waste.

FIG. 2 illustrates one embodiment of the injection system suitable for continuous injections of the base into the waste installed in a waste storage facility. A tank 20 is provided to hold a suitable quantity of the base solution and is connected with a pump 22. The pump 22 is connected with a valve 24 that controls the flow of the base solution to the rest of the injection system. The pump 22 and valve 24 are motorized so that they may be remotely controlled by the controller 14. At least one pipe 26 travels from the valve 24 to points around the waste storage facility. At multiple points along the pipe 26, injector assemblies 28 are installed. Each injector assembly includes a metering nozzle 30 and an injector 32. The metering nozzle 30 meters the flow of the base solution to the injector 32, while the injector 32 delivers the base solution into the waste present in the facility.

Figure 3:
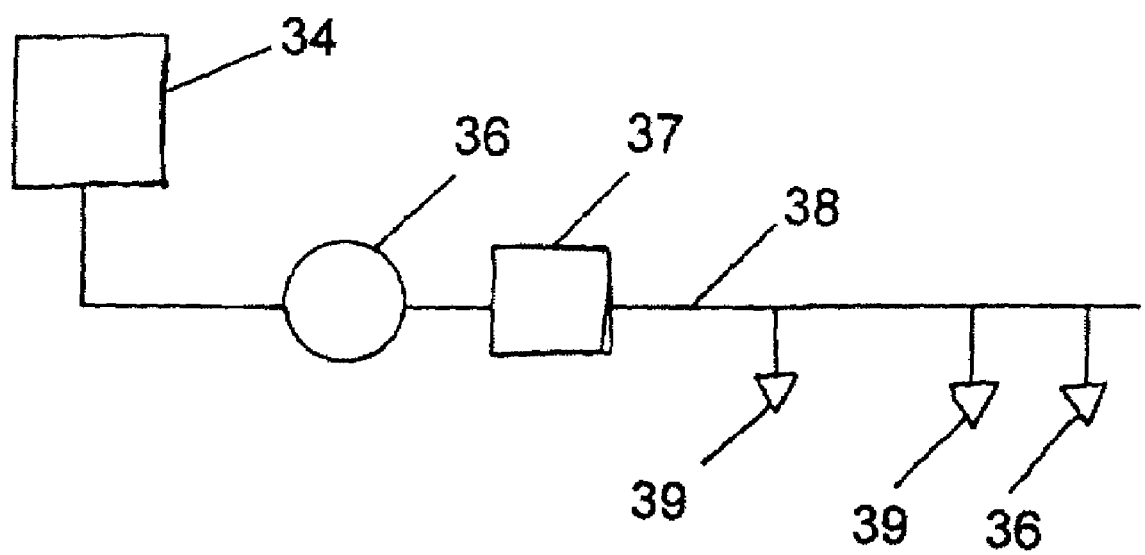
FIG. 3 is a schematic view of a delivery system suitable for applying an oil seal as part of a method for treating digestible and odiferous waste.

A delivery system for the oil seal is illustrated in FIG. 3. A tank 34 is provided to store the material for the oil seal and is connected with a pump 36. The pump 36 is connected with a valve 38 that controls the flow of the oil seal to the rest of the delivery system. The pump 36 and valve 37 are motorized so that they may be remotely controlled by the controller 14. At least one pipe 38 travels from the valve 37 to points around the waste storage facility at a level above the usual level of the waste. At multiple points along the pipe 38, nozzles 39 are installed to deliver the oil seal to the surface of the waste. The nozzles 39 are advantageously arranged to allow the oil seal material to be dispensed from the nozzles and flow down the walls of the containment system to the waste surface, thereby minimizing any agitation of the waste.

Figure 4:
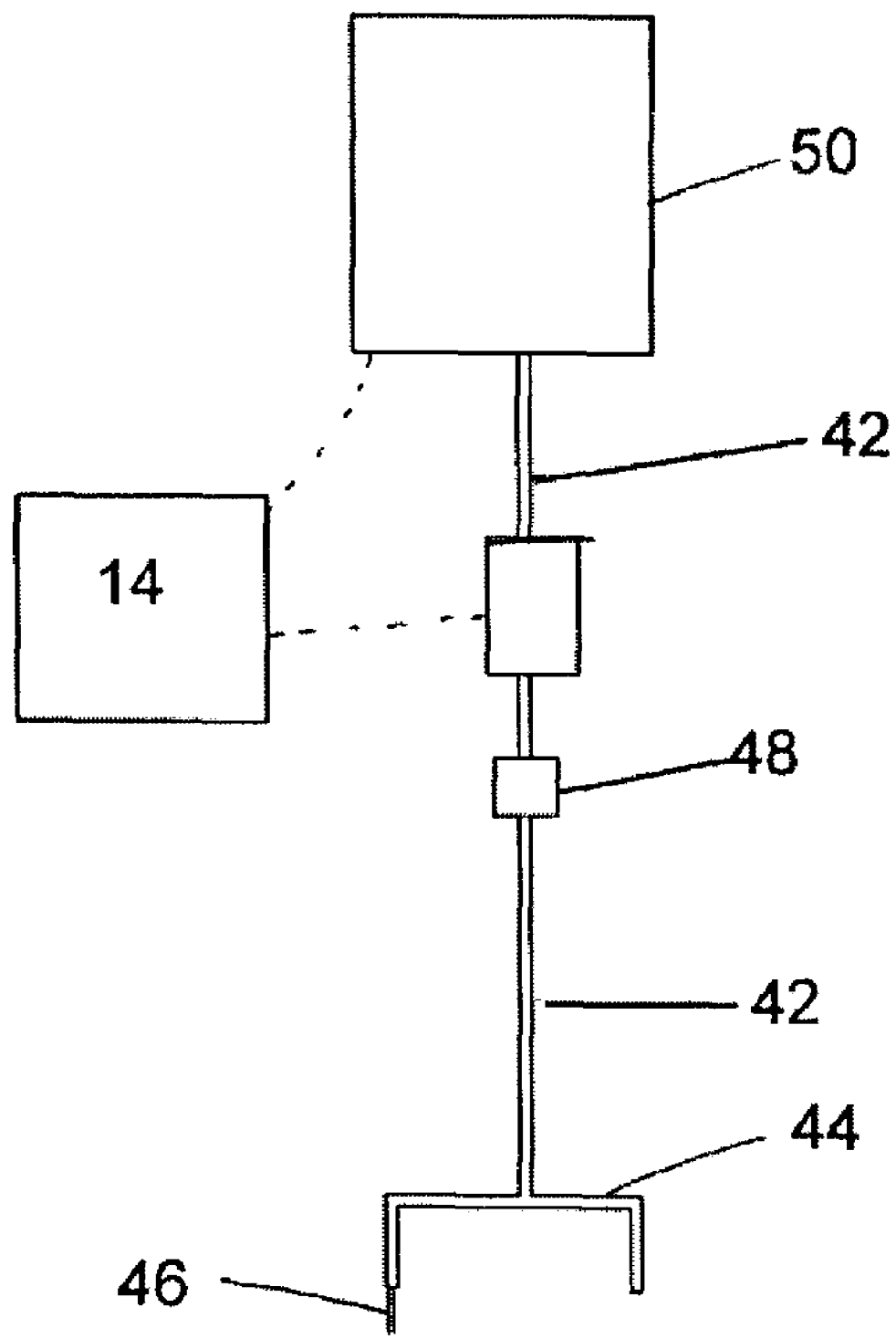
FIG. 4 is a schematic view of a self-cleaning pH monitor suitable for use with the system of FIG. 1.

FIG. 4 illustrates a particularly advantageous pH monitor for use with the system. Upper 40 and lower 42 shafts are mounted to a support surface. The lower shaft 42 extends into the waste pit and is provided with a forked structure 44 at the end inserted into the waste pit. A pH sensor 46 is connected to one branch of the forked structure 44, while the other branch is capped. A coupler 48 connects the upper 40 and lower 42 shafts, both structurally and electrically. If the lower shaft 42 encounters an obstruction that prevents it from rotating, the coupler 48 disconnects the two shafts, thereby allowing the upper shaft 40 to continue rotating while preventing the lower shaft 42 from dropping into the waste pit. A motor 50 is mounted to the support surface and is connected with, and acts on, the top of the upper shaft 40. The motor 50 is preferably controlled by the controller 14. In a preferred embodiment, the motor is $\frac{1}{20}^{th}$ HP gear motor with 113 in·lbs. of available torque. A swivel electrical communicator 52, which includes a commutator, is associated with the upper shaft 40 and electrically connects the upper shaft 40 to the controller 14. Both of the shafts are preferably made of stainless steel pipe, allowing the shafts to electrically connect the pH sensor 46 to the controller 14.

As the motor 50 rotates the shafts 40, 42 and the forked structure 44, the pH sensor 46 is moved in a circular pattern through the waste. The rotation of the forked end 44 prevents a waste film from forming on the pH sensor 46, which impairs its accuracy, by creating sufficient friction with the surrounding waste to "scrape" the sensor clean. The second branch of the forked structure 44 serves to help clear potential obstructions as the structure rotates. A debris deflector (not shown) may also be mounted upstream of the forked structure 44 to limit any obstructions from striking the pH sensor 46. The controller 14 controls the rotation of the sensor 46. In one preferred embodiment of the system, the sensor 46 is rotated for ten seconds of every hour at a speed of approximately 6 rpm.

The following tests illustrate the effectiveness of an embodiment of the odor control method. Samples were tested in an environment that simulated conditions found in animal storage facilities. Two testing rooms of equal size and air space were provided for testing. One sample was poured and left untreated as a base-line or control sample, and another sample of equal volume and surface area was treated in accordance with the above description. The samples were contained in a rectangular tray. Raw swine waste extracted from a finishing barn was used for the samples to produce the odors. A depth of 1.5 inches of waste was applied in each tray. After applying the treatment to the surface of said other sample, the prepared samples were left to stand for four minutes. Then each sample was placed in the center of the designated room for the purpose of creating an air sample to be tested initially by smell. In the room where the untreated sample was left, odors were detected immediately upon entering the room. In the room containing the treated sample, no odors were detected in the presence of the sample; indeed the room appeared to smell the same as before the treated sample was placed therein.

The samples were left in the testing areas for 24 hours and once again the rooms were monitored for the presence of odor. In the room where the untreated sample was left, the odors were still present at an unacceptable level. In the room where the treated sample was left, there was no odor present that was detectable by the human nose.

Figure 5:
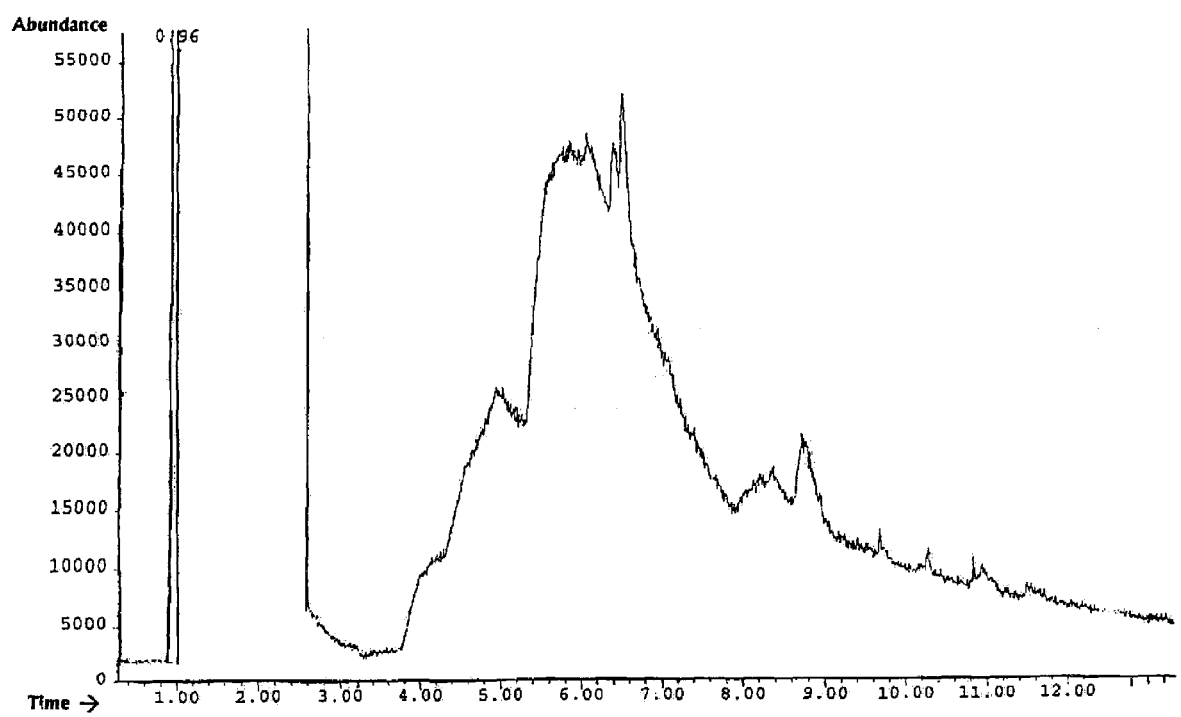
FIG. 5 is a chromatograph of a head space air sample collected above an untreated portion of a concentrated fatty acid solution

Further testing was conducted using gas chromatography-mass spectroscopy (GS-MS) to detect the presence of odiferous compounds in an enclosed headspace 24 hours after treatment. Several pure volatile fatty acids, i.e., acetic acid, propionic acid, butanoic acid, hexanoic acid and heptanoic acid, were mixed together with small amounts of water to produce an aqueous solution far more concentrated in volatile fatty acids than in animal waste slurry. Because of the high concentration of these fatty acids in aqueous solution, the same acids could be detected by gas chromatography-mass spectroscopy in the headspace above the liquid sample. FIG. 5 shows the results collected from the sealed headspace above an untreated portion of the concentrated acid solution. The greater the area under a peak shown in FIG. 5, the higher the concentration of the compound being detected in the headspace. The signals recorded beyond 3.5 minutes are due to acetic acid (4.0-5.0 min.), propionic acid (4.5-5.5 min.), butanoic acid (5.5-8.0 min.) and hexanoic acid (7.0-10 min.). Heptanoic acid was not detected in the headspace. The signal before 3.0 minutes, which goes off the chart shown in FIG. 3, is due to argon and carbon dioxide. Both argon and carbon dioxide are minor components of the natural air we breath. Thus, the graph in FIG. 5 demonstrates how low in concentration the fatty acids are, even above a very concentrated solution. However, even a relatively low concentration of fatty acids in the headspace may create a highly offensive odor and potentially dangerous odorous emissions.

Figure 6:
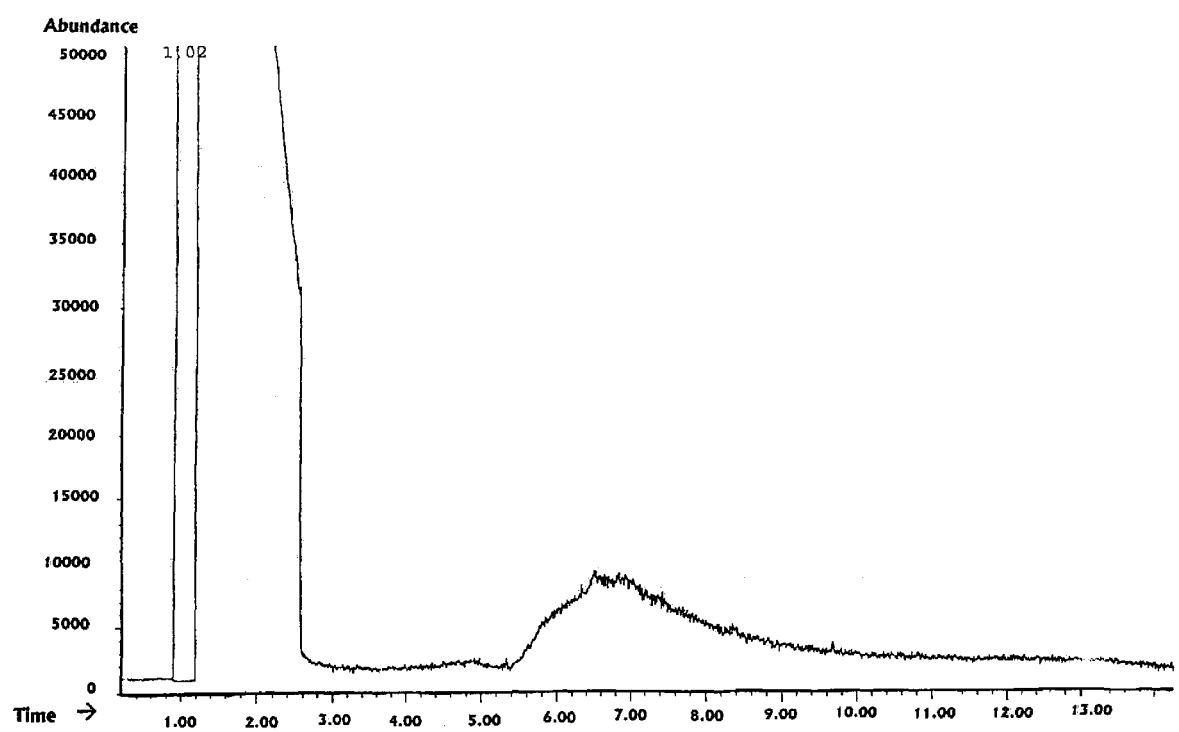
FIG. 6 is a chromatogram of a head space air sample collected above a concentrated fatty acid solution covered with one inch of an oil.

FIG. 6 is the chromatogram of a sample collected above the same concentrated fatty acid solution, now covered with one inch of corn oil alone, and shows the reduction in the areas under the peaks for all the fatty acids.

Figure 7:
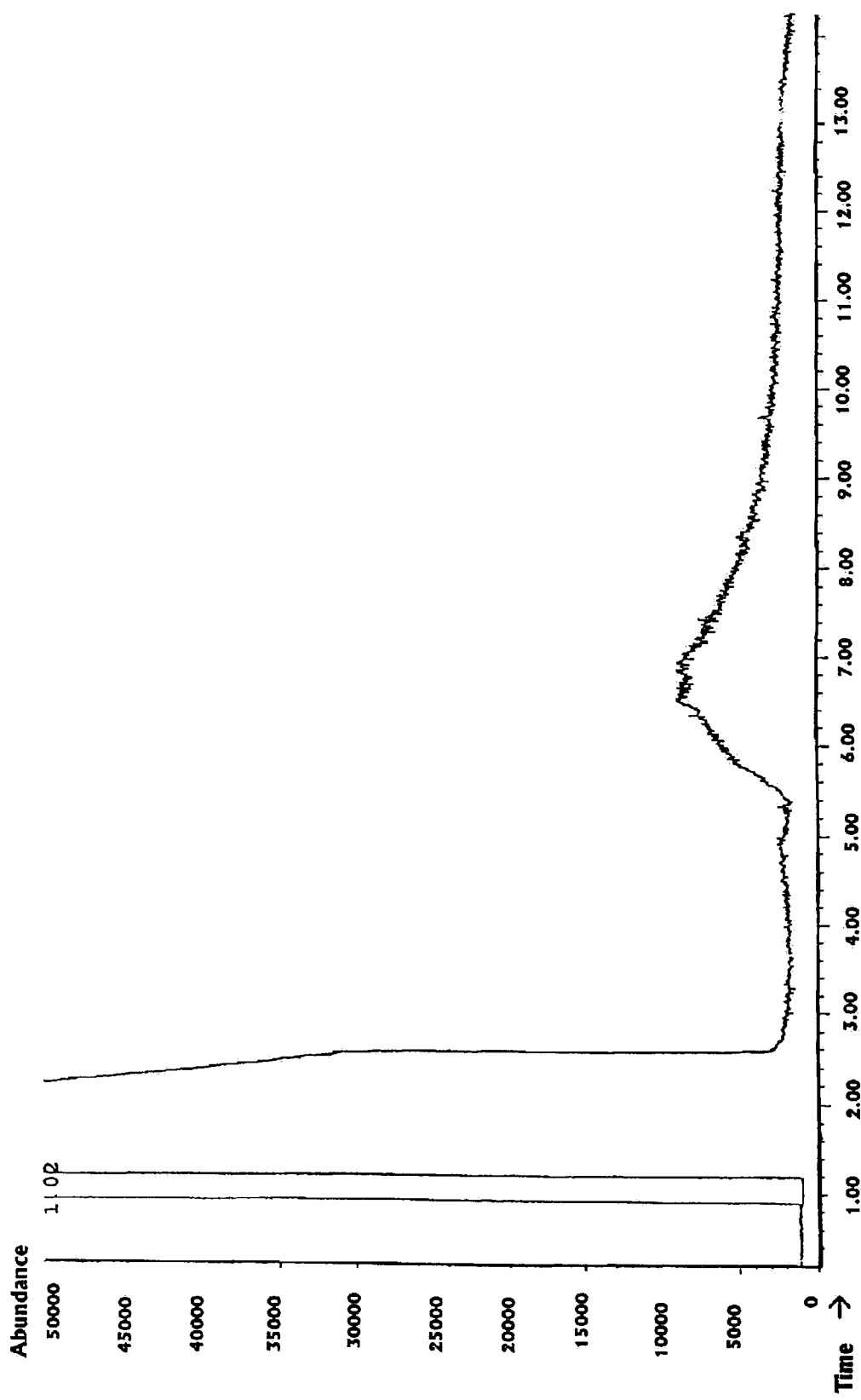
FIG. 7 is a chromatogram of a head space air sample collected above a concentrated fatty acid solution covered with one inch of an oil containing activated carbon

FIG. 7 is the chromatogram of a sample collected above the same fatty acid solution, now covered with one inch of the same oil as in the FIG. 6 sample but containing activated carbon in an oil to carbon ratio of approximately 5:1. While oil to activated carbon ratio of 5:1 was used in this particular test, subsequent tests have utilized a ratio of 128:1 with similar results. Once again, it can be seen that the concentration of fatty acids in the headspace above the liquid waste is diminished even further than the sample having only oil applied and the untreated sample.

Figure 8:
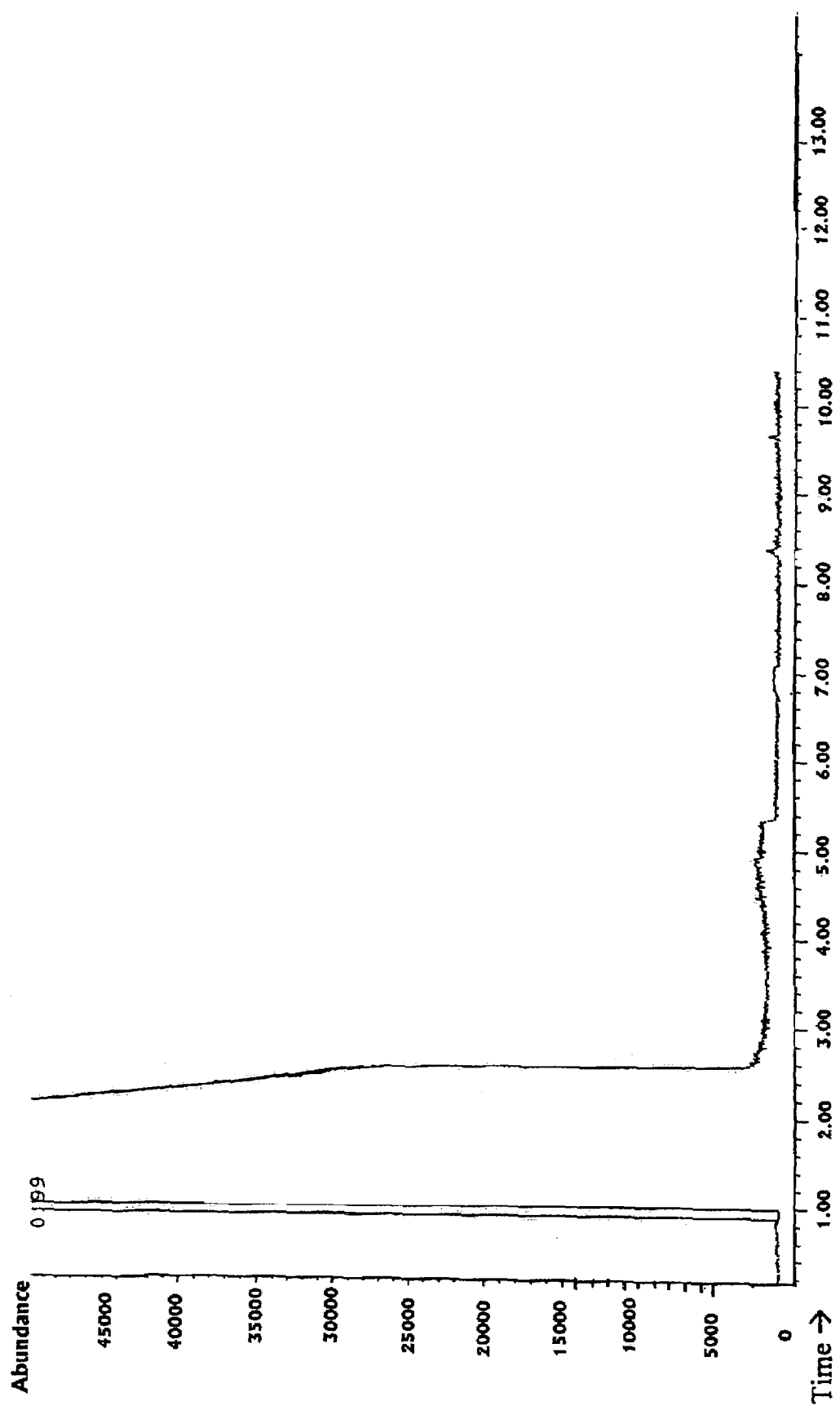
FIG. 8 is a chromatogram of a head space air sample collected above a concentrated fatty acid solution covered with one inch layer of oil containing activated carbon and treated with an ammonia base buffering agent.

FIG. 8 is the chromatogram of a sample collected with the same fatty acid solution covered with a one inch layer of the same oil and activated carbon as in the FIG. 7 sample, and further treated with an ammonia base buffering agent. This chromatogram also shows the progression of diminishing concentrations of the fatty acids in the headspace above the liquid waste, to the point where the fatty acids are undetectable in FIG. 8.

Figure 9:
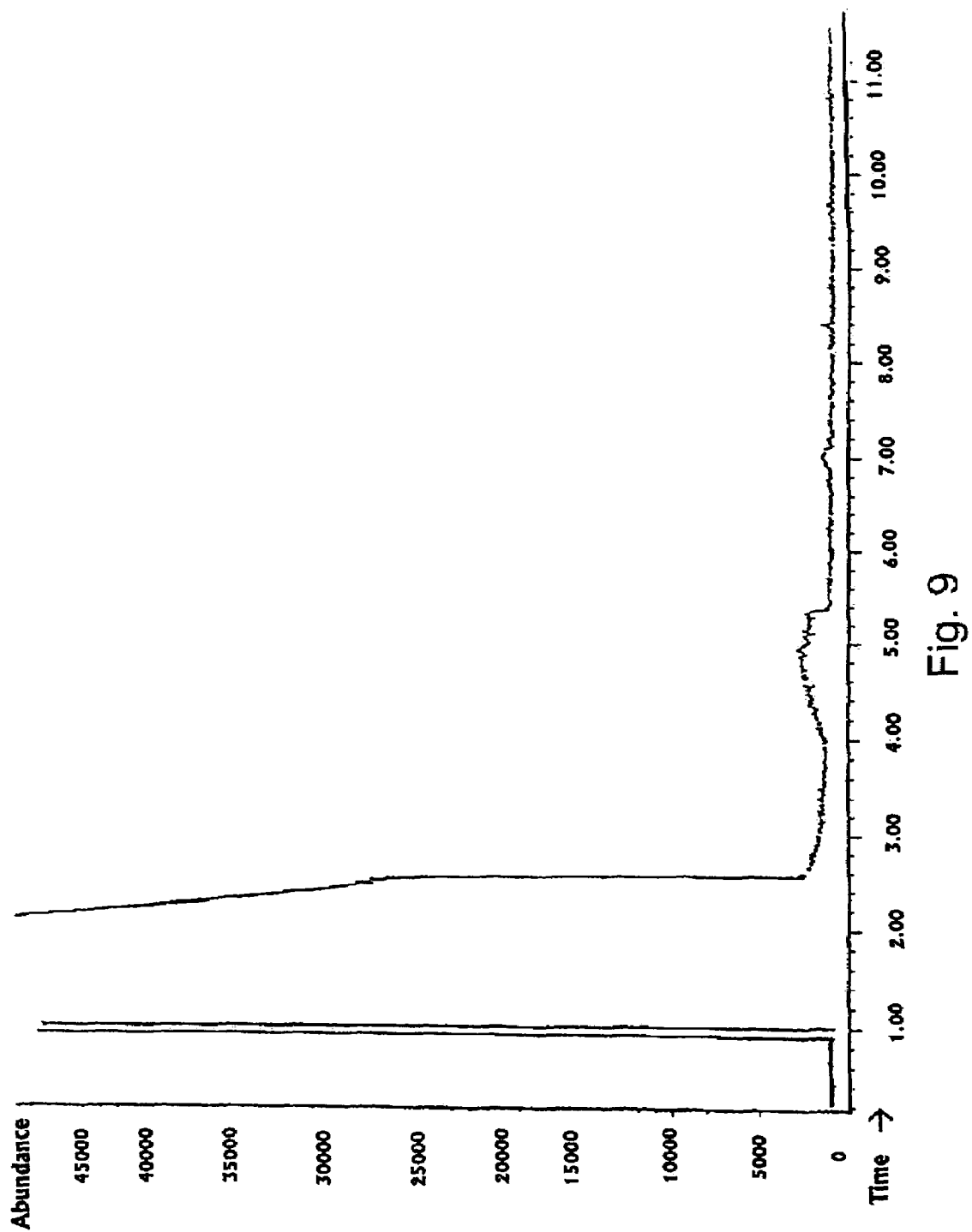
FIG. 9 is a chromatograph of ordinary air with no waste sample present.

As another base-line or control test, FIG. 9 shows a chromatograph of a sample of ordinary air with no waste sample present. This test remarkably shows that the emissions for the treated sample, shown in FIG. 8, are virtually identical to those of regular laboratory air.

It should be understood that the alkaline solution in the above description encompasses embodiments including ammonia and water and embodiments including ammonia, an ammonium salt and water, as well as equivalents thereof.

Furthermore, the alkaline solution may encompass unspecified trace elements that are generally found in typical water sources.

Other objects, features and advantages will be apparent to those skilled in the art. The invention in its broader aspects is not limited to the specific steps and apparatus shown and described but departures may be made therefrom within the scope of the appended claims without departing from the principles of the invention and without sacrificing the chief advantages.

What is claimed is:

1. A method of treating digestible and odiferous animal waste in a containment system to minimize odors, including the step of adding an alkaline solution into the digestible and odiferous animal waste to at least partially neutralize volatile fatty acids present in the digestible and odiferous animal waste, wherein the step of adding an alkaline solution includes using a mixture of about 7.2% ammonia, about 3.2% ammonium chloride, and the remainder water as the alkaline solution.

2. A method of treating digestible and odiferous animal waste in a containment system to minimize odors, including the steps of adding an alkaline solution into the digestible and odiferous animal waste to at least partially neutralize volatile fatty acids present in the digestible and odiferous animal waste, and applying a layer of oil to the surface of the digestible and odiferous animal waste, wherein the step of applying a layer of oil includes applying a mixture of oil and activated carbon, wherein the ratio of oil to activated carbon in the layer of oil is about 128:1.

3. A method of treating digestible and odiferous animal waste in a containment system to minimize odors including the steps of:
holding the digestible and odiferous waste in a containment system so that the waste has an upper surface;
preparing a mixture of activated carbon and corn oil in a ratio of about 1:128;
applying a layer of the corn oil and activated carbon mixture onto the upper surface of the digestible and odiferous waste and to a depth of at least about one quarter inch; and
adding an alkaline solution including about 7.2% ammonia into the digestible and odiferous animal waste below the level of the corn oil and activated carbon mixture.

4. A method of treating digestible and odiferous animal waste in a containment system to minimize odors as set forth in claim 3, wherein the step of adding an alkaline solution includes using a mixture of about 7.2% ammonia, about 3.2% ammonium chloride, and the remainder water as the alkaline solution.

5. A method of treating digestible and odiferous animal waste in a containment system, including the step of reacting volatile fatty acids present in the digestible and odiferous animal waste with an alkaline solution to create an acid/base reaction and at least partly neutralize the volatile fatty acids to neutral salts, wherein the step of reacting volatile fatty acids with an alkaline solution includes using a mixture of about 7.2% ammonia, about 3.2% ammonium chloride, and the remainder water as the alkaline solution.

6. A method of treating digestible and odiferous animal waste in a containment system, including the step of reacting volatile fatty acids present in the digestible and odiferous animal waste with an alkaline solution to create an acid/base reaction and at least partly neutralize the volatile fatty acids to neutral salts, and further including the step of forming a seal of at least one quarter inch in depth over the surface of the digestible and odiferous animal waste composed of a mixture of oil and activated carbon, wherein the ratio of activated carbon to oil is about 1:128.

7. The use of a layer of oil and activated carbon in conjunction with an alkaline solution in amounts suitable to control odors from digestible and odiferous animal waste in a containment system including the steps of applying the layer of activated carbon and oil to the surface of the digestible and odiferous animal waste in a ratio of approximately 1:128 and adding the alkaline solution into the digestible and odiferous animal waste below the surface thereof and in an amount to maintain an alkaline, anaerobic environment.

8. The use as set forth in claim 7, wherein the alkaline solution is added in an amount to maintain an alkaline, anaerobic environment having a pH level in the range of about 7.5 to 8.0.

9. The use as set forth in claim 7, wherein the oil is a vegetable oil.

10. The use as set forth in claim 7, wherein the oil is corn oil.

11. The use as set forth in claim 7, wherein the alkaline is composed of a mixture of about 3.2% ammonium salt, about 7.2% ammonia, and the remainder water.

12. The use as set forth in claim 7, wherein the alkaline solution is a mixture of about 7.2% ammonia and the remainder water.

* * * * *